US00PP27322P2

(12) United States Plant Patent
Joyce

(10) Patent No.: US PP27,322 P2
(45) Date of Patent: Nov. 1, 2016

(54) RED BAYBERRY PLANT NAMED 'N1MR06'

(50) Latin Name: *Myrica rubra*
Varietal Denomination: N1MR06

(71) Applicant: The University of Queensland, St Lucia (AU)

(72) Inventor: Daryl Clifford Joyce, Karalee (AU)

(73) Assignee: The University of Queensland, Queensland (AU)

( * ) Notice: Subject to any disclaimer, the term of this patent is extended or adjusted under 35 U.S.C. 154(b) by 27 days.

(21) Appl. No.: 14/120,614

(22) Filed: Jun. 9, 2014

Related U.S. Application Data

(63) Continuation of application No. 13/506,807, filed on May 16, 2012, now abandoned.

(51) Int. Cl.
*A01H 5/08* (2006.01)

(52) U.S. Cl.
USPC ..... Plt./156

(58) Field of Classification Search
USPC ..... Plt./156, 226
See application file for complete search history.

*Primary Examiner* — June Hwu
(74) *Attorney, Agent, or Firm* — Klarquist Sparkman, LLP

(57) ABSTRACT

A new and distinct cultivar of Red Bayberry, botanically known as *Myrica rubra*, and hereinafter referred to by the name 'N1MR06' is described. 'N1MR06' produces fruit having improved sweetness, a good sugar:acid ratio, a palatable low resin taste along with uniform fruit size and colour. N1MR06 has the following traits: mean fruit diameter is 21.4 mm; mean fruit weight is 5.87 g; fruit colour is red-black; mean fruit flesh total soluble solids (an indicator of sweetness) is 12.0° Brix; mean fruit flesh titratable acidity is 1.41%; and fruit harvest season in the southern hemisphere is early-mid November.

1 Drawing Sheet

Botanical denomination: *Myrica rubra.*
Variety designation: 'N1MR06'.

BACKGROUND TO THE INVENTION

The present invention relates to a new and distinct cultivar of Red Bayberry, botanically known as *Myrica rubra*, and hereinafter referred to by the name 'N1MR06'.

'N1MR06' is the product of a selection program started by the inventor in 2002 in a cultivated area of Knoxfield, Victoria, Australia. The primary focus of the selection program is to produce new cultivars of Red Bayberry with fruit having improved sweetness, a good sugar:acid ratio, a palatable low resin taste along with uniform fruit size and colour.

'N1MR06' was selected in 2008 from a mature planting of twelve cutting-propagated genotypes which the inventor had originally grown from out-crossed seed collected from China. The inventor is unable to identify either the male or the female parent. A later planting comprising 141 seedlings from a second batch of seed were evaluated for fruit quality in 2010. The combination of traits displayed by 'N1MR06' was not found in any of the 141 seedlings. Hence, 'N1MR06' is considered to be a unique cultivar.

SUMMARY OF THE INVENTION

The cultivar 'N1MR0' was asexually reproduced by clonal propagation, using cuttings or by grafting onto rootstock in Gatton, Queensland, Australia. The original clonal propagation to produce the variety was conducted via vegetative tip cuttings.

The cultivar 'N1MR06' has not been tested under all possible conditions and phenotypic differences may be observed with variations in environmental, climatic and cultural conditions, without however any change in genotype.

The following traits have been observed and represent the characteristics of the new *Myrica rubra* cultivar 'N1MR06'. These traits in combination distinguish 'N1MR06' from all other varieties of *Myrica rubra* known to the inventor.

1. Mean fruit diameter is 21.4 mm.
2. Mean fruit weight is 5.87 g.
3. Fruit colour is red-black.
4. Mean fruit flesh total soluble solids (an indicator of sweetness) is 12.0° Brix.
5. Mean fruit flesh titratable acidity is 1.41%.
6. Fruit harvest season in the southern hemisphere is early-mid November.

DETAILED BOTANICAL DESCRIPTION

Figure 1:
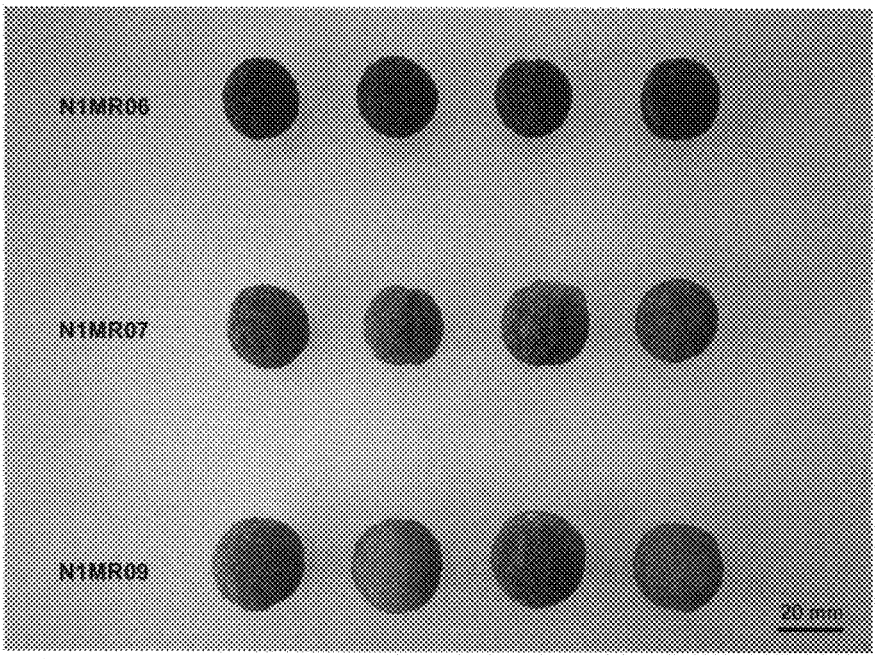
FIG. 1 is a digital image showing representative fruit of 'N1MR06', 'N1MR07', and 'N1MR09' displaying the variation in fruit size, shape and colour; harvested November 2011 in Nambour, Queensland, Australia.
Figure 2:
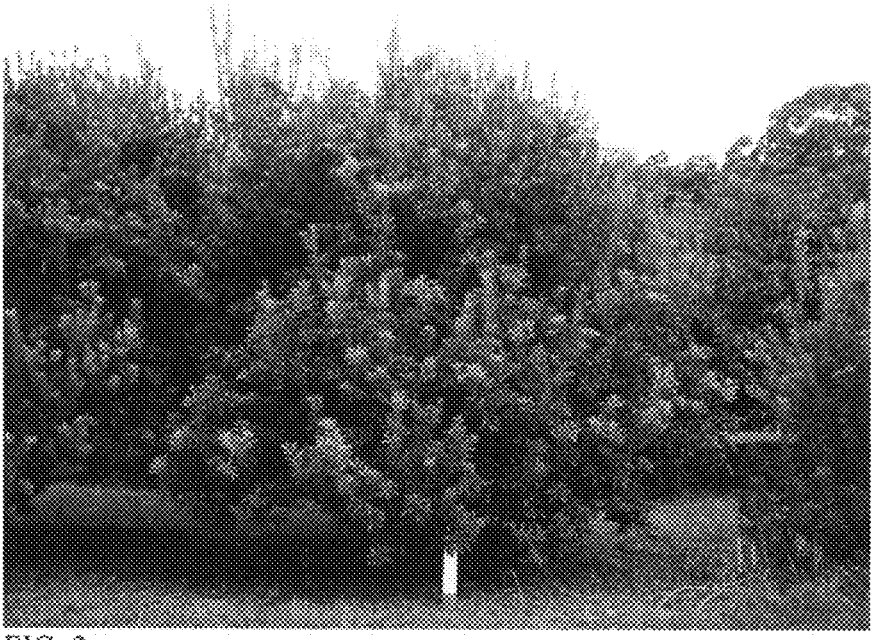
FIG. 2 is a digital image showing the whole plant of 'N1MR06' in Nambour, Queensland, Australia.

The following description describes the *Myrica rubra* cultivar 'N1MR06' at 7 years. The vegetative propagule was observed in a test plot maintained with standard management practices for commercial bayberry production in Nambour, Queensland, Australia. Certain characteristics of this variety, such as growth and colour, may change with changing environmental conditions (e.g., light, temperature, moisture, nutrient availability, or other factors). Colour descriptions and other terminology are used in accordance with their ordinary dictionary descriptions, unless the context clearly indicates otherwise. Colour designations are based on the CIE L.C.h colour model and were measured using a Konica Minolta CR-400 Chroma Meter.

Botanical classification: *Myrica rubra.*

Parentage:

*Female parent plant.*—Unknown.

*Male parent plant.*—Unknown.

Plant:

*Vigor.*—General observations of 'N1MR06' plantings indicate average plant vigor.

*Plant habit.*—Branched shrub, elongate in shape; can be limbed up into a multi-trunked small tree.

*Plant dimensions.*—Height 3.6 m, Width 3.4 m.

*Plant hardiness.*—USDA Zone 9 (potentially ranging from 8 to 10).

*Type.*—Evergreen shrub.

*Disease resistance.*—No disease resistance data available for foliar or root pathogens.

Fruit:

*Shape.*—Spherical.

*Size.*—In Nambour, Queensland, Australia, average diameter was 21.4 mm.

*Skin.*—Knobby (papillate).

*Colour.*—Red-black. CIE L.C.h color measurements are as follows: Lightness (L)=17.99±0.26; Chroma (C)=19.60±0.78; Hue (h)=14.54±0.33.

*Weight.*—In Nambour, Queensland, Australia, average weight was 5.87 g.

*Number of seeds.*—One.

*Flesh.*—Pink-red.

*Fruit chemistry.*—Samples of fruit were harvested from test plots in Nambour, Queensland, Australia and evaluated for fruit chemistry. Average fruit flesh total soluble solids were 12.0° Brix and average fruit flesh titratable acidity was 1.41%.

*Fruit production.*—Early — mid November.

Leaf:

*Length (mm).*—95.6±1.5.

*Width (mm).*—29.50±0.5.

*Shape.*—Oblanceolate.

*Margin type.*—Entire.

*Texture (upper surface).*—Glabrous.

*Texture (lower surface).*—Glabrous.

*Fragrance.*—Mildly fragrant when bruised.

*Color (upper surface).*—139A (Light=32; Chroma=16; hue=146).

*Color (lower surface).*—147B (Light=47; Chroma=21; hue=112).

*Apex shape.*—Acute to obtuse, rarely retuse.

*Base shape.*—Cuneate.

Leaf bud:

*Axillary bud length (mm).*—3.13±0.09.

*Axillary bud shape.*—Ovoid to ovoid-conical.

*Axillary bud number per axil.*—1.10±0.07.

*Axillary bud colour.*—165C (Light=67; Chroma=38; hue=65).

Petiole:

*Length (mm).*—9.07±0.23.

*Surface texture.*—Glabrous.

*Color.*—152D (Light=62; Chroma=46; hue=88).

Stem:

*Shape.*—Round.

*Surface texture.*—Woody.

*Presence/absence of lenticel.*—Present.

*Color.*—N199A (Light=38; Chroma=15; Hue=76).

Flower:

*Monoecious or dioecious.*—Dioecious.

*Flower form.*—Incomplete, lacks petals and sepals.

*Flowering season.*—Late winter to early spring.

*Flower colour.*—None, flowers are apetalous.

*Average number of flowers per inflorescence.*—13.96±4.686.

*Average inflorescence length.*—15.98 mm±0.86.

*Size.*—Very small and inconspicuous.

Peduncle:

*Average peduncle length.*—4.54 mm±1.435.

Reproductive organs:

*Number of pistils per flower.*—2. The variety produces pistillate flowers only.

Seeds:

*Length (mm).*—10.60±0.14.

*Width (mm).*—8.63±0.12.

*Thickness (mm).*—7.27±0.12.

*Shape.*—Broad elliptic to broad obovate.

*Color.*—165D (Light=78; Chroma=31; hue=71).

Shipping and storage characteristics: Fruit decay severity after 15 d storage at 5° C.: slight. This data is preliminary (based on fruit harvested from a single location) and may have been affected by environmental conditions.

Pollination requirement: Dioecious. Cross-pollination by wind.

TABLE 1

Comparison of characteristics of 'N1MR06', 'N1MR07', and 'N1MR09'

| Characteristic | 'N1MR09' | 'N1MR06' | 'N1MR07' |
|---|---|---|---|
| Tree: habit | spreading | semi-upright | upright |
| Tree: compactness | standard | compact | standard |
| Tree: vigour | medium to strong | strong | strong |
| Leaf blade: length | medium | medium | medium |
| Leaf blade: width | broad | broad | medium |
| Leaf blade: ratio length/width | small | medium | medium |
| Leaf blade: shape of tip | blunt acute | blunt acute | blunt acute |
| Leaf blade: shape in cross section | concave | concave | concave |
| Leaf blade: green colour of upper side | medium | dark | medium |
| Leaf: attitude in relation to shoot | upwards | upwards | upwards |
| Fruit: size | medium | medium | large |
| Fruit: firmness of flesh | medium | firm | soft to medium |
| Fruit: total soluble solids of juice | high | high | medium |
| Fruit: acid content of juice | high | high | medium |
| Time of: beginning of flowering | early | medium | medium |
| Time of: fruit maturity | early | early | medium |
| Fruit: Skin protruberances | moderate | moderate | moderate |
| Fruit: Uniformity of protruberances | even | even | uneven |
| Fruit: Colour of flesh | pink-white | pink-red | pink-white |
| Fruit: Drop or shed before harvest | high | low | low |
| Shoot: internode length | medium | medium | long |
| Leaf: Colour - underside of leaf | light green | light green | very light green |
| Leaf: Undulating margin | slightly undulating | undulating | slightly undulating |
| Shoot : Size of lenticels | large | medium | large |

TABLE 1-continued

Comparison of characteristics of 'N1MR06', 'N1MR07', and 'N1MR09'

| Characteristic | 'N1MR09' | 'N1MR06' | 'N1MR07' |
|---|---|---|---|
| Shoot: Density of lenticels | sparse | dense | medium |
| Flower: Number of flowers per inflorescence | medium | high | high |
| Fruit: Colour of skin | light | dark | medium |
| Fruit: Yield | medium | medium | high |
| Leaf: Number of buds per leaf axil | multiple | mainly single | single |
| Leaf: Petiole length | medium | medium | medium |
| Fruit: Resinous taste | absent | absent | absent |
| Shoot: Colour of juvenile shoot | black red | black red | black red |
| Shoot: Colour of juvenile leaf tips | dark red | medium red | dark red |
| Flower: Peduncle length | medium | long | medium |
| Fruit: Seed weight | medium | low | medium |

TABLE 2

Comparison of characteristics of 'N1MR06' and *Morella rubra* cv. 'Biqi'

| Characteristic | 'N1MR06' | 'Biqi' |
|---|---|---|
| Tree: habit | semi-upright | semi-upright |
| Tree: compactness | compact | standard |
| Tree: vigour | strong | strong |
| Leaf blade: length | medium | medium |
| Leaf blade: width | broad | narrow |
| Leaf blade: ratio length/width | medium | large |
| Leaf blade: shape of tip | blunt acute | blunt acute |
| Leaf blade: shape in cross section | concave | concave |
| Leaf blade: green colour of upper side | dark | dark |
| Leaf: attitude in relation to shoot | upwards | upwards |
| Fruit: size | medium | medium |
| Fruit: firmness of flesh | firm | medium |
| Fruit: total soluble solids of juice | high | medium |
| Fruit: acid content of juice | high | medium |
| Time of: beginning of flowering | medium | early |
| Time of: fruit maturity | early | medium |
| Fruit: Skin protruberances | moderate | strong |
| Fruit: Uniformity of protruberances | even | even |
| Fruit: Colour of flesh | pink-red | pink-white |
| Fruit: Resinous taste | absent | present |
| Fruit: Drop or shed before harvest | low | low |
| Shoot: internode length | medium | medium |
| Shoot : Size of lenticels | medium | small |
| Shoot: Density of lenticels | dense | medium |
| Shoot: Colour of juvenile shoot | black red | red |
| Leaf: Colour - underside of leaf | light green | light green |
| Leaf: Undulating margin | undulating | slightly undulating |
| Leaf: Colour of juvenile leaf tips | medium red | medium red |
| Flower: Peduncle length | long | medium |
| Flower: Number of flowers per inflorescence | high | medium |
| Fruit: Colour of skin | dark | medium |
| Fruit: Yield | medium | high |
| Leaf: Number of buds per leaf axil | mainly single | single |
| Leaf: Petiole length | medium | high |
| Fruit: weight of seed | low | high |

TABLE 3

Comparison of characteristics of 'N1MR06', 'N1MR07', and 'N1MR09'

| Morphological characteristic | Genotype N1MR06 | N1MR07 | N1MR09 |
|---|---|---|---|
| Leaf length (mm) | 95.6 ± 1.5 | 100.4 ± 2.1 | 91.1 ± 1.5 |
| Leaf width (mm) | 29.50 ± 0.5 | 29.87 ± 0.62 | 27.97 ± 0.56 |
| Leaf shape | oblanceolate | oblanceolate | oblanceolate |

TABLE 3-continued

Comparison of characteristics of 'N1MR06', 'N1MR07', and 'N1MR09'

| Morphological characteristic | Genotype N1MR06 | N1MR07 | N1MR09 |
|---|---|---|---|
| Leaf margin type | entire | entire | entire |
| Leaf texture (upper surface) | glabrous | glabrous | glabrous |
| Leaf texture (lower surface) | glabrous | glabrous | glabrous |
| Leaf fragrance | mildly fragrant when bruised | mildly fragrant when bruised | mildly fragrant when bruised |
| Leaf colour (upper surface) | 139A (Light = 32; Chroma = 16; hue = 146) | 139A (Light = 32; Chroma = 16; hue = 146) | 139A (Light = 32; Chroma = 16; hue = 146) |
| Leaf colour (lower surface) | 147B (Light = 47; Chroma = 21; hue = 112) | 147B (Light = 47; Chroma = 21; hue = 112) | 147B (Light = 47; Chroma = 21; hue = 112) |
| Leaf apex shape | acute to obtuse, rarely retuse | acute to obtuse, rarely retuse | acute to obtuse, rarely retuse |
| Leaf base shape | cuneate | cuneate | cuneate |
| Axillary bud length (mm) | 3.13 ± 0.09 | 2.63 ± 0.10 | 4.50 ± 0.12 |
| Axillary bud shape | ovoid to ovoid-conical | ovoid to ovoid-conical | ovoid to ovoid-conical |
| Axillary bud number per axil | 1.10 ± 0.07 | 1.00 ± 0.00 | 5.20 ± 0.22 |
| Axillary bud colour | 165C (Light = 67; Chroma = 38; hue = 65) | 153D (Light = 72; Chroma = 58; hue = 88) | 165C (Light = 67; Chroma = 38; hue = 65) |
| Number of scales per leaf bud | could not be determined | could not be determined | could not be determined |
| Petiole length | 9.07 ± 0.23 | 9.20 ± 0.37 | 10.27 ± 0.24 |
| Petiole surface texture | glabrous | glabrous | glabrous |
| Petiole colour | 152D (Light = 62; Chroma = 46; hue = 88) | 152D (Light = 62; Chroma = 46; hue = 88) | 152D (Light = 62; Chroma = 46; hue = 88) |
| Stem shape | round | round | round |
| Stem surface texture | woody | woody | woody |
| Presence/absence of lenticel on stem | present | present | present |
| Stem colour | N199A (Light = 38; Chroma = 15; Hue = 76) | N199A (Light = 38; Chroma = 15; Hue = 76) | 199B (Light = 54; Chroma = 20; hue = 74) |
| Monoecious or dioecious | dioecious | dioecious | dioecious |
| Flower form | incomplete, lacks petals and sepals | incomplete, lacks petals and sepals | incomplete, lacks petals and sepals |
| Flowering season | late winter to early spring | late winter to early spring | late winter to early spring |
| Flower colour | none, flowers are apetalous | none, flowers are apetalous | none, flowers are apetalous |
| Number of stamens per flower | species is dioecious, variety produces pistillate flowers only | species is dioecious, variety produces pistillate flowers only | species is dioecious, variety produces pistillate flowers only |
| Number of pistils per flower | 2 | 2 | 2 |
| Stamen size | species is dioecious, variety produces pistillate flowers only | species is dioecious, variety produces pistillate flowers only | species is dioecious, variety produces pistillate flowers only |
| Stamen colour | species is dioecious, variety produces pistillate flowers only | species is dioecious, variety produces pistillate flowers only | species is dioecious, variety produces pistillate flowers only |

TABLE 3-continued

Comparison of characteristics of 'N1MR06', 'N1MR07', and 'N1MR09'

| Morphological characteristic | Genotype | | |
|---|---|---|---|
| | N1MR06 | N1MR07 | N1MR09 |
| Pollen colour | species is dioecious, variety produces pistillate flowers only | species is dioecious, variety produces pistillate flowers only | species is dioecious, variety produces pistillate flowers only |
| Seed length (mm) | 10.60 ± 0.14 | 12.13 ± 0.16 | 12.23 ± 0.13 |
| Seed width (mm) | 8.63 ± 0.12 | 9.30 ± 0.13 | 10.03 ± 0.14 |
| Seed thickness (mm) | 7.27 ± 0.12 | 8.63 ± 0.10 | 8.63 ± 0.10 |
| Seed shape | broad elliptic to broad obovate | broad elliptic to broad obovate | broad elliptic to broad obovate |
| Seed colour | 165D (Light = 78; Chroma = 31; hue = 71) | 165D (Light = 78; Chroma = 31; hue = 71) | 165D (Light = 78; Chroma = 31; hue = 71) |

TABLE 3-continued

Comparison of characteristics of 'N1MR06', 'N1MR07', and 'N1MR09'

| Morphological characteristic | Genotype | | |
|---|---|---|---|
| | N1MR06 | N1MR07 | N1MR09 |
| Fruit decay severity after 15 d storage at 5° C. | slight | severe | moderate |

Quantitative data are provided as means ± standard error of the mean for n = 30 samples. Leaf and petiole measurements were conducted on mature, fully expanded leaves harvested at shoulder height. Vegetative and floral axillary buds are identical in appearance until bud burst or leaf expansion becomes evident. Hence, no distinction is made between the type of axillary bud.

Colour measurements were made using the Royal Horticultural Society Colour Chart (5th edition) and converted to CIE LCh values using online tables at rhscf.orgfree.com (accessed 10 Mar. 2016). Seed measurements were conducted on seed with intact endocarp (i.e., the stone)

The invention claimed is:

1. A new and distinct variety of red bayberry plant, substantially as illustrated and described herein.

* * * * *